(12) United States Patent
Rodier

(10) Patent No.: US 6,945,090 B2
(45) Date of Patent: Sep. 20, 2005

(54) METHOD AND APPARATUS FOR MONITORING MOLECULAR CONTAMINATION OF CRITICAL SURFACES USING COATED SAWS

(75) Inventor: Daniel Rodier, Louisville, CO (US)

(73) Assignee: Particle Measuring Systems, Inc., Boulder, CO (US)

(*) Notice: Subject to any disclaimer, the term of this patent is extended or adjusted under 35 U.S.C. 154(b) by 159 days.

(21) Appl. No.: 10/178,699

(22) Filed: Jun. 24, 2002

(65) Prior Publication Data

US 2003/0233864 A1 Dec. 25, 2003

(51) Int. Cl.$^7$ .............................................. G01N 29/02
(52) U.S. Cl. ..................... 73/24.06; 73/31.03; 73/579
(58) Field of Search ............................ 324/71.2; 73/579, 73/589, 590, 24.01, 24.04, 24.06, 24.05, 54.24, 54.25, 54.26, 54.27, 61.49, 64.53, 1.82, 31.06

(56) References Cited

U.S. PATENT DOCUMENTS

| | | | | |
|---|---|---|---|---|
| 3,253,219 A | * | 5/1966 | Littler | ......................... 324/71.1 |
| 5,321,331 A | * | 6/1994 | Baer et al. | ............... 310/313 D |
| 5,627,749 A | * | 5/1997 | Waterman et al. | ........... 364/422 |
| 5,795,993 A | | 8/1998 | Pfeifer et al. | ............... 73/24.01 |
| 5,856,198 A | * | 1/1999 | Joffe et al. | ................... 436/100 |
| 5,859,537 A | * | 1/1999 | Davis et al. | ................. 324/693 |
| 5,918,258 A | | 6/1999 | Bowers | |
| 6,079,252 A | * | 6/2000 | Tabler et al. | .................... 73/40 |
| 6,122,954 A | | 9/2000 | Bowers | |
| 6,378,370 B1 | * | 4/2002 | Haskell et al. | ................. 73/579 |
| 6,490,927 B2 | * | 12/2002 | Braunling et al. | ............. 73/579 |

* cited by examiner

*Primary Examiner*—Charles D Garber
(74) *Attorney, Agent, or Firm*—Patton Boggs LLP

(57) ABSTRACT

A molecular contamination monitor for monitoring molecular contamination on a surface of a subject surface susceptible to degradation by a molecular contaminant. The monitor includes a surface acoustic wave (SAW) device having a SAW measurement surface coated with a material that is equivalent to the subject material with respect to spontaneous contamination by a contaminant. In the preferred embodiment, the coating comprises the same material as the subject surface or a material that interacts chemically with the contaminant in an equivalent manner to the subject surface. Exemplary coatings include: photoresist, copper, silver, gold, platinum, titanium, tungsten, aluminum, nickel, metal oxides, stearic acid, silicon, gallium arsenide, gallium nitride, germanium, silicon germanium, silicon dioxide, silicon nitride, and glass. Exemplary coating methods include sputtering, CVD, ALD and misted deposition.

16 Claims, 7 Drawing Sheets

METHOD AND APPARATUS FOR MONITORING MOLECULAR CONTAMINATION OF CRITICAL SURFACES USING COATED SAWS

BACKGROUND OF THE INVENTION

1. Field of the Invention

The invention relates to real-time monitoring of molecular gas-solid surface, chemical, and physical interactions for purposes including detection of airborne molecular contaminants pertaining to manufacturing and processing environments.

2. Statement of the Problem

Many manufacturing processes and technologies are susceptible to airborne or gas-phase molecular contaminants (AMC), and to the related surface molecular contamination (SMC) resulting from chemical interactions between AMC and critical surfaces exposed to same. Such critical surfaces, called "subject surfaces" herein, are, for example: integrated circuit surfaces, such as resist, silicon and other semiconductors; wiring surfaces made of tungsten, aluminum, or other metals; silicon dioxide surfaces; optical surfaces; mechanical surfaces; surfaces of hard disks; surfaces of flat panel displays; etc. Detrimental effects of SMC include, for example, changes in the chemical, electrical, and optical qualities of critical surfaces. These detrimental effects decrease product performance and reliability, and raise product cost. Some examples of such detrimental effects to the above-mentioned critical surfaces include T-topping of resist, defective epitaxial growth, unintentional doping, uneven oxide growth, changes in wafer surface properties, corrosion and decreased metal pad adhesion. Many of these are becoming particularly detrimental as line widths less than 0.18 microns are being used. Further, as wafer size increases and device geometry decreases, the demand for more sensitive monitoring techniques will increase. In the optics industry, SMC is a well-known cause of hazing of optical surfaces. SMC also causes striction problems in certain mechanical devices, such as hard disk drives, since SMC contaminated surfaces may have a significantly higher coefficient of friction than uncontaminated surfaces. SMC also affects the manufacture of hard disk drives and flat panel displays which, for reasons known in the art, are typically carried out in a plurality of "mini" clean rooms.

The various AMCs causing detrimental SMC may be grouped into four general categories, which are: acids, bases, condensables, and dopants, otherwise referred to as SEMI F21-95 Classes A, B, C and D. Some AMCs, though, are of no particular class.

Sources for AMC include inadequate filtration of recirculated air, cross-process chemical contamination, outgassing of cleanroom materials, such as filters, gel sealants and construction materials, as well as contaminants carried in and exhuded by human beings. When the fluid is outdoor "make-up" air, the sources of AMC include automobile exhaust, evapotranspiration from plants, and various industrial emissions. The AMC also includes chemical compounds and vapors resulting from chemical breakdown of, and interaction between, the molecules within the AMC from the primary sources. Other sources of AMC/SMC include cross-process chemical contamination within a bay or across a facility, and recirculated air with inadequate ventilation. Still other sources include outgassing by cleanroom materials, such as filters, gel sealants, and construction materials, especially new fabrics, and various contaminants emanating from industrial equipment, such as pumps, motors, robots and containers. Another source is accidents, including chemical spills, and upsets in temperature and humidity controls. Still another source is people, including their bodies, clothes, and their personal care products.

AMC can cause yield losses even when present at concentrations as low as the low parts per billion by volume ("ppbv"). Such processes therefore require an ultra-clean, well-monitored environment.

No single monitoring instrument or technology is capable of monitoring across the four categories of AMC. Most existing technology instead focuses on subsets of the AMC categories, or particular species of AMC within one of the categories.

Another shortcoming of the existing monitoring technologies is that most monitor airborne, or ambient suspension, concentrations of AMC. Quartz crystal microbalances (QCM) and existing surface acoustic wave (SAW) technologies monitor SMC, but only on the surface of the QCM or SAW. Monitoring of accumulated SMC on the surface of the QCM crystal or SAW substrate may not provide accurate measurement of, or insight into, the chemical interactions at a critical surface. One significant reason for this failure is that the nature of the chemical interactions between the AMCs and the subject surface depends not only on the airborne or ambient concentration of the AMC, but on other factors such as the extent and nature of other AMC on the surface, temperature and relative humidity and, of notable importance, the chemical makeup of the critical surface. Therefore, when air samples are evaluated for AMC, the measured concentrations are converted to estimated quantities of molecular contamination on the subject surfaces. Typically, the estimation is based on sample duration or exposure time and the deposition rate:

$$S = E(NV/4), \qquad (1)$$

where

S is the deposition rate in molecules/cm squared/sec;

E is a dimensionless sticking coefficient having a value ranging between 0 and 1;

N is the number density in air in molecules per cm cubed; and

V is the average thermal velocity in cm per second.

E depends on temperature, humidity, surface composition, and the magnitude and type of other AMC present. E can only be derived experimentally and it is different for virtually every situation. Thus, it is recognized as a consistent and significant source of error.

The only commercially available approach that attempts to provide this data is the QCM. However, QCMs typically operate between 4 MHz and 12 MHz. SAWs typically operate at frequencies of 200 MHz and higher. Mass sensitivity of piezoelectric devices, both QCM and SAW, is proportional to the square of the frequency. QCM mass sensitivity is therefore, conservatively, two orders of magnitude poorer than that of a SAW mass. The lower mass sensitivity translates to poorer time resolution of mass change events, such as SMC accumulating on the QCM crystal as a result of an AMC event. Stated differently, if a SAW and a QCM device are exposed to the same AMC concentration, the SAW device has a rate of frequency change approximately two orders of magnitude higher than the QCM device. Therefore, the QCM must be exposed longer than the SAW to exhibit the same frequency change. This may effectively blur or miss contamination events that happen on short time scales. For this reason, QCM technology does not have sufficient mass sensitivity for adequate monitoring of critical surfaces exposed to short duration AMC. One such example is the monitoring of photoresists for exposure ammonia and amines, which may occur only over a two-hour period.

SAW devices have been used for detecting molecular contamination. See U.S. Pat. No. 6,122,954 issued Sep. 26, 2000 and U.S. Pat. No. 5,918,258 issued Jun. 29, 1999, both to William D. Bowers. In these devices, a fluid containing a contaminant is brought into contact with the SAW under conditions that promote deposition of the contaminant on the SAW, such as by evaporation of the fluid to leave the contaminants, or by covering the SAW with a hydroscopic polymer to enhance absorption of water, in cases where water is a contaminant. However, the first method is slow, and the second is limited both by types of contaminants that may be detected and reuseability of the SAW.

SOLUTION

The present invention advances the art and overcomes the aforementioned problems by providing a SAW coated with a surface that mimics the critical surface that is subject to contamination, i.e., the subject surface. For example, if the subject surface is the copper surface of a hard disk element, then the SAW is coated with copper. The SAW output then may be used to monitor the surface contamination of a copper surface of a hard disk element that is exposed to the same environment. As another example, if the subject surface is a surface susceptible to corrosion by acidic gas, a silver coated SAW may be used to monitor the corrosion, since silver is highly susceptible to corrosion by acidic gases. As another example, a stearic acid coated SAW may be used to mimic a subject surface that is susceptible to degradation by ammonia, since stearic acid itself is degraded by ammonia.

The present invention provides high sensitivity, real-time monitoring of the aggregate impact of AMC on critical subject surfaces, and by substantially reducing, if not eliminating, reliance on estimated sticking coefficients and related estimation of SMC on critical surfaces. The sensitivity and stability of this inventive SAW device provides high frequency surface and AMC sampling, and provides correlation between the data and local process events. Further, the present inventive SAW device provides substantially improved mass sensitivity, thereby permitting monitoring of new types of surfaces that cannot be effectively monitored with a QCM.

The invention also provides a method of manufacturing an AMC monitor comprising the coating of a SAW surface with a thin film. Here, the term "thin film" is used as it is used in the integrated circuit art, meaning a film of less than a micron in thickness. The coating may be done using sputtering, chemical vapor deposition (CVD), atomic layer deposition (ALD) or misted deposition.

The invention provides a device for monitoring molecular contamination on a surface of a subject surface susceptible to degradation by a molecular contaminant, the device comprising: a surface acoustic wave (SAW) device having a SAW measurement surface, the SAW device including an electrical circuit for providing an output signal indicative of a contaminant on the measurement surface; and the SAW measurement surface including a coating that is equivalent to the subject material with respect to spontaneous contamination by a contaminant. Preferably, the coating comprises essentially the same material as the subject surface. Alternatively, the coating comprises a material that interacts chemically with the contaminant in an equivalent manner to the subject surface. Preferably, the coating is a photoresist. Preferably, the coating is metallic, the SAW includes a transducer, the coating overlays the transducer, and the molecular contamination monitor includes an insulating film disposed between the transducer and the coating such that the coating is not in electrical contact with the transducer. Preferably, the coating comprises a material selected from the group consisting of copper, silver, gold, platinum, titanium, tungsten, aluminum and nickel. Preferably, the coating comprises a metal oxide. Preferably, the coating comprises a semiconductor material. Preferably, the coating comprises a material selected from the group consisting of silicon, gallium arsenide, gallium nitride, germanium, and silicon germanium. Preferably, the coating comprises a material selected from the group consisting of silicon dioxide, silicon nitride, and glass. Preferably, the coating comprises stearic acid. Preferably, the coating comprises a thin film.

The invention also provides a method of manufacturing a device for monitoring molecular contamination on a surface of a subject surface susceptible to degradation by a molecular contaminant, the method comprising: providing a surface acoustic wave (SAW) device having a SAW measurement surface; and coating the SAW measurement surface with a detector material that is equivalent to the subject material with respect to spontaneous contamination by a contaminant. Preferably, the act of coating comprises sputtering. Preferably, the act of coating comprises chemical vapor deposition. Preferably, the act of coating comprises atomic layer deposition. Preferably, the act of coating comprises misted deposition. Preferably, the act of coating comprises: providing a liquid precursor containing chemical elements in amounts suitable for forming the detector material; and using the liquid precursor to form the coating. Preferably, the liquid precursor comprises an alkoxide, a metal alkyl, a beta-diketonate or a carboxylate.

In another aspect, the invention provides a method of manufacturing a device for monitoring molecular contamination, the method comprising: providing a surface acoustic wave (SAW) device having a SAW measurement surface; and sputtering a detector coating on the SAW measurement surface.

In a further aspect, the invention provides a method of manufacturing a device for monitoring molecular contamination, the method comprising: providing a surface acoustic wave (SAW) device having a SAW measurement surface; and using atomic layer deposition to form a detector coating on the SAW measurement surface.

In still another aspect, the invention provides a method of manufacturing a device for monitoring molecular contamination, the method comprising: providing a surface acoustic wave (SAW) device having a SAW measurement surface; and using chemical vapor deposition to form a coating on the measurement surface.

In yet another aspect, the invention provides a method of manufacturing a device for monitoring molecular contamination, the method comprising: providing a surface acoustic wave (SAW) device having a SAW measurement surface; and using misted deposition to form a coating on the measurement surface.

In yet a further aspect, the invention provides a method of manufacturing a device for monitoring molecular contamination, the method comprising: providing a surface acoustic wave (SAW) device having a SAW measurement surface; providing a liquid precursor containing chemical elements in amounts suitable for forming a detector material; and using the liquid precursor to form a coating of the detector material on the SAW measurement surface. Preferably, the liquid precursor comprises an alkoxide, a metal alkyl, a beta-diketonate or a carboxylate.

The invention for the first time provides a practical device for monitoring molecular contamination. Numerous other features, objects and advantages of the invention will become apparent from the following description when read in conjunction with the accompanying drawings.

DETAILED DESCRIPTION OF THE PREFERRED EMBODIMENT

The term "fluid" is defined herein as a liquid or gas, or a vapor mixture, including air, elemental gasses such as nitrogen and argon, and mixtures of the same. When an example operation is described, the particular fluid used for the description is not, unless otherwise stated or clear from the context, intended as a limitation on the scope or operation of the invention.

Figure 1:
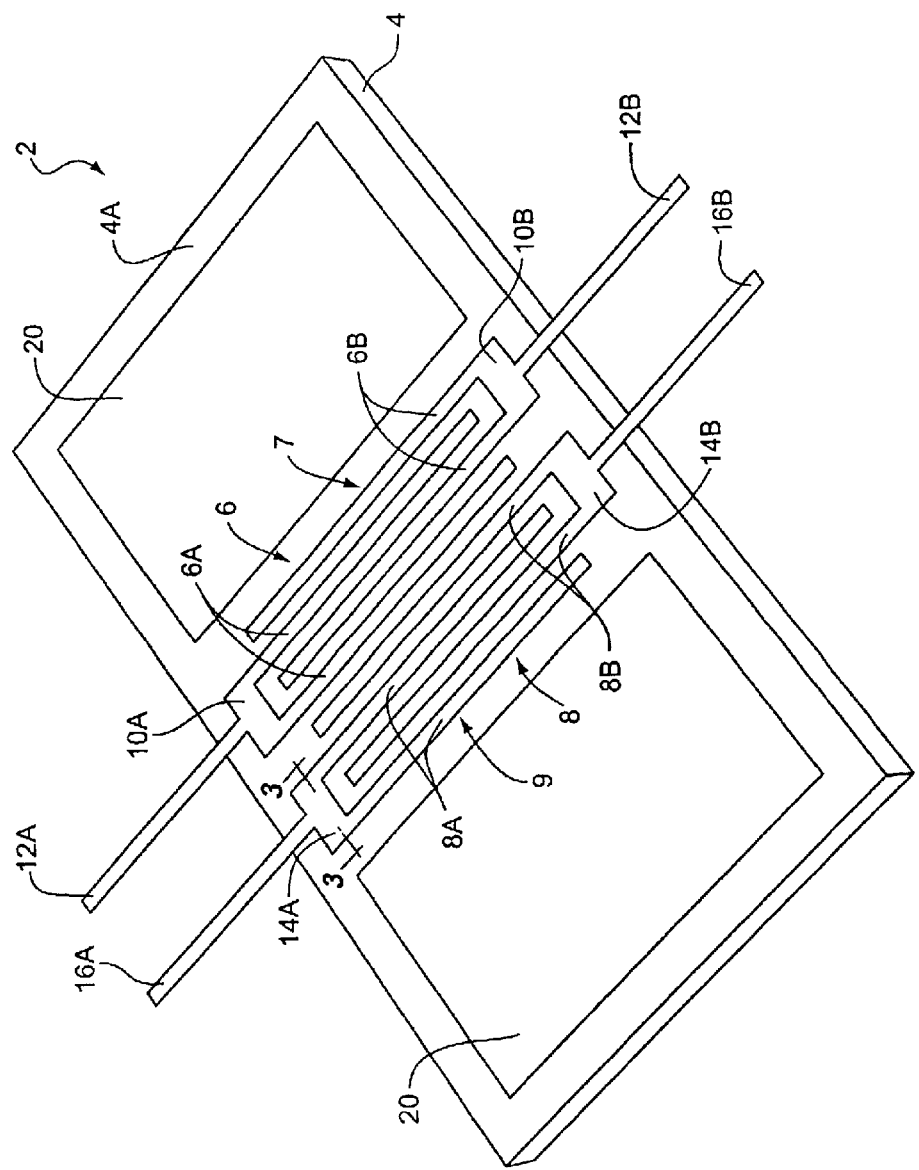
FIG. 1 is a perspective view of an example SAW device according to the present invention.

FIG. 1 shows an example equivalent surface SAW apparatus 2 according to a first aspect of this invention. The FIG. 1 example equivalent surface SAW apparatus 2 comprises a substrate 4 having a measurement surface 4A, with a first pair 6 of interdigital transducers, labeled 6A and 6B respectively, disposed on a first area 7 of surface 4A. A second pair 8 of interdigital transducers, labeled 8A and 8B respectively, is disposed on a second area 9 of surface 4A. A first contact pad 10A connects to transducer 6A of the first pair and to a first connection line 12A. Similarly, a second contact pad 10B connects to transducer 6B of the first pair and to a second connection line 12B. A third contact pad 14A connects to transducer 8A of the second transducer pair and to a third connection line 16A. A fourth contact pad 14B connects to transducer 8B of the second transducer pair and to a fourth connection line 16B.

A coating or thin film 20 is disposed on surface 4A over an area in which surface acoustic waves propagate in response to electric signals input to one or more of the first transducer pair 6A, 6B and the second transducer pair 8A, 8B, as described below. The film 20 changes the acoustic wave propagation velocity as compared to a substrate 4 without a coating on its surface 4A.

For this aspect of the invention, the film 20 comprises an equivalent material to the critical surface to be monitored, which is preferably the same material as that of the critical surface to be monitored. Here, "equivalent material" means a material that mimics the critical surface with respect to spontaneous contamination by a contaminant. The contamination is spontaneous in that it occurs naturally in the same manner as does the contamination of the critical surface, as contrasted to contamination by manipulation such as pouring a sample of contaminated fluid on the surface and then evaporating it as in the prior art. As molecular contamination absorbs to the surface or reacts with the surface of the film 20 to form new molecules, the mass on the surface increases. The increased mass further affects the acoustic wave propagation velocity and changes the wavelength of an acoustic wave at a given frequency. Since the film 20 is of the same material as the critical surface, the reactivity of the film 20 and resultant new molecules provide a detection surface which is selective to molecular contaminants reactive to the critical surface.

The term "thin film" is used herein in the way it is used in the integrated circuit art. It means a film of less than a micron in thickness, and preferably of 0.5 micron or less. Typically, the thin film thickness may range from, for example, 1 nm to 100 nm, with the thickness depending, in part, on the sensing application in which the device will be used. As a general guideline, the thickness preferably corresponds to the thickness of the critical surface for which AMC is being monitored. For example, if the critical surface is a 5 nm film, then the test film would preferably be 5 nm. If the critical surface is a 50 nm film, then the test film thickness would preferably be approximately 50 nm. However, if the test film thickness is too high, the mass sensitivity will be reduced. It should be understood that the them "thin film" does not include the so-called "thin films" of the macroscopic arts, such as discrete capacitors. In these arts, while the film is "thin" as compared to films lay persons use everyday, they are hundreds if not thousands of times thicker than films used routinely in the integrated circuit art, and the processes of making the films are inherently entirely different.

Example films 20 include, but are not limited to: copper, silver, gold, platinum, titanium, tungsten, aluminum, nickel, metal oxides and alloys, gallium arsenide, gallium nitride, semiconductors, metal oxides, photoresists, all types of glass, silicon dioxide, polymers, stearic acid, and various other coatings specific to particular industries, technologies, and processes. If the film 20 is a non-conductor such as, for example, a polymer, it can be applied across the entire surface 4A. Metallic films 20 can cover surface 4A except for contact pads 10A, 10B, 14A and 14B. Preferably, a nonconductive layer is applied to the contact pads beforehand if a metal is to be applied over these pads.

Figure 3:
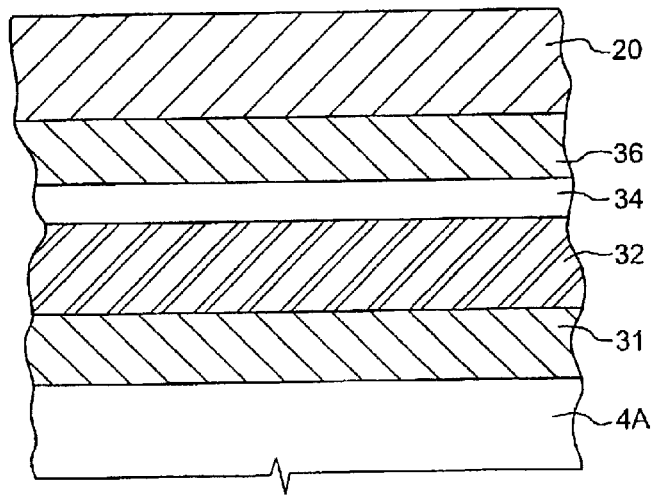
FIG. 3 is a cross-sectional view of the SAW measurement surface 4A in the vicinity of a contact pad taken through the line 3—3 of FIG. 1.

The film 20 may be deposited directly on measurement surface 4A. However, in many instances, it will be preferable to have an intermediate layer of material, or several intermediate layers, between surface 4A and layer 20. These layers may include a passivation layer, a barrier layer, an insulating layer, or an adhesion layer. This is illustrated in FIG. 3. FIG. 3 is a cross-section through the area of a contact pad 14A. In this area, a contact pad metal layer 31 is deposited on surface 4A. A passivation layer 32 is generally deposited over the entire surface 4A. This layer also acts as an insulating layer between contact 31 and detection surface 20. A barrier layer 34, for example, a layer of silicon nitride, may be formed on passivation layer 32. An adhesion layer 36 is formed on insulating layer 34, and detection material 20, which is equivalent to a critical surface, is formed on adhesion layer 36. Layers 32, 34 and 36 are optional and are shown to illustrate that the invention contemplates that passivation, insulating, barrier and adhesion layers as may be necessary to make layer 20 effective, stable and reliable in its function are preferably included. For example, if detection surface layer 20 is platinum, a passivation/insulating layer 34 of CVD deposited silicon dioxide, alumina ($Al_2O_3$), or silicon nitride may be used to insulate the platinum from contact layer 32, followed by a thin adhesion layer 36 of sputtered titanium, since platinum does not adhere well to some materials, such as silicon dioxide. In this case, the silicon dioxide also acts as passivation layer 32 and the titanium adhesion layer 36 together with the silicon dioxide passivation layer 32 together act as a barrier.

Thin film layer 20 may be formed by sputtering, chemical vapor deposition (CVD), atomic layer deposition (ALD), misted deposition or any other suitable process. The preferred method of application for metals is ion beam sputtering onto a masked SAW surface. This gives a good surface. One exemplary method for applying polymer coatings is chemical vapor deposition. Another method is misted deposition with small droplets of a dilute solution of polymer in a volatile solvent, such as 2-methoxyethanol. The coating can be done as a single layer or in multiple layers.

A suitable chemical vapor deposition process is described in International Patent Publication No. WO 99/02756 published Jan. 21, 1999 on an application of Paz de Araujo et al., and a suitable misted deposition process is described in U.S. Pat. No. 5,997,642 issued Dec. 7, 1999 to McMillan et al., both of which are incorporated by reference as though fully disclosed herein. These processes begin with the providing of a liquid precursor having chemical elements suitable for forming the detection material. Liquid precursors that have been found useful are alkoxides, metal alkyls, beta-diketonates, and carboxylates dissolved in a solvent. Suitable solvents include methyl ethyl ketone, isopropanol, methanol, tetrahydrofuran, xylene, n-butyl acetate, hexamethyl-disilazane (HMDS), octane, 2-methoxyethanol, and ethanol. The liquid precursor is applied to the substrate. If it is applied via a CVD process, the coated substrate may be used without further treatment, though preferably it is annealed at a temperature of from 500° C. to 800° C. after coating. If it is applied via a misted deposition process, the liquid coating is dried at a temperature of from 150° C. to 300° C. and then annealed in a furnace at a temperature of from 500° C. to 800° C. Alternatively, a rapid thermal anneal, known in the art as RTA or RTP, may be used.

Sputtering and ALD are well-known in the integrated circuit art.

Figure 2:
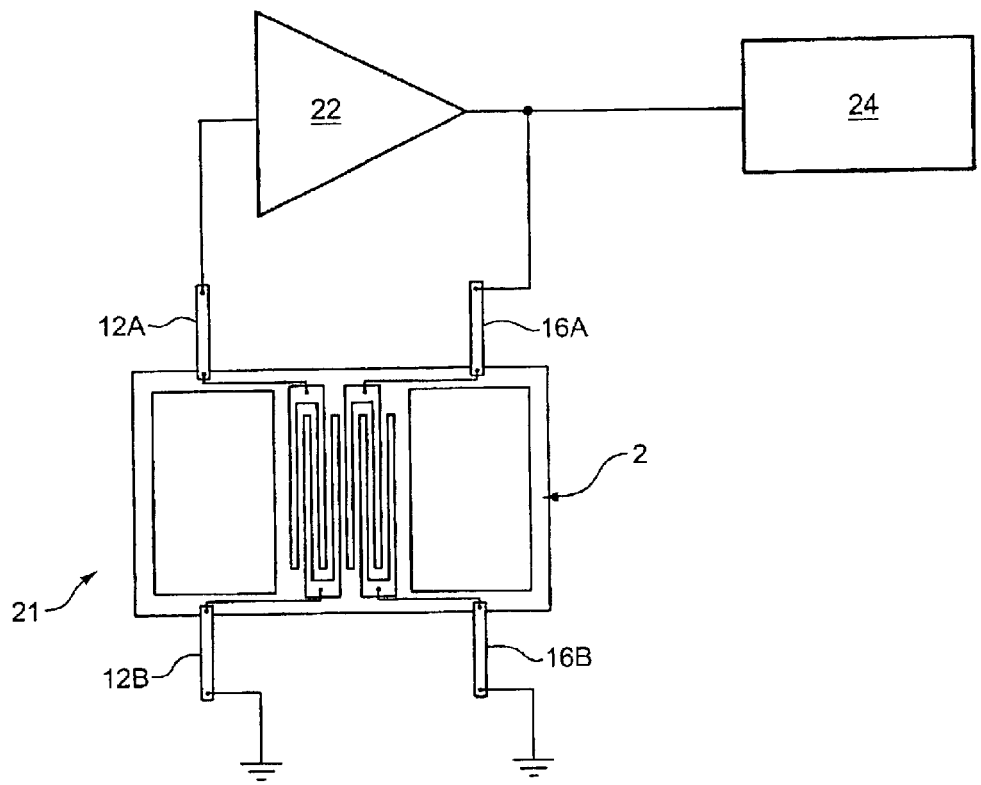
FIG. 2 shows an example reactive detection apparatus having a SAW device according to the FIG. 1 example.

FIG. 2 shows an example reactive surface SAW measurement apparatus having the FIG. 1 reactive surface SAW 2 connected within a free-running oscillator circuit 21. Connecting the SAW 2 within a free-running oscillator 21 is one of the methods for detecting changes in the film 20 mass contemplated by this invention. The FIG. 2 circuit forms a free-running oscillator circuit 21 by connecting the first and second transducer pair 6A, 6B and 8A, 8B, respectively, to an amplifier 22 as shown in FIG. 2, which is known in the prior art of SAW-based AMC detectors. Amplifier 22 may contain phase-shifting elements for desired oscillation characteristics, as is also known in the art. The oscillating frequency depends, in part, on the acoustic wave propagation velocity. The change in acoustic wave propagation velocity caused by increased mass of the film 20 due to new molecules formed by interaction with molecular contamination therefore changes the oscillating frequency. The change in oscillator frequency is detected by the frequency detector 24. It will be understood that the free-running oscillator depicted by FIG. 2 is merely an example, as other SAW-based oscillator circuits are known in the art. Further details of a SAW detector circuit are given in U.S. Pat. No. 6,122,954 issued Sep. 26, 2000 to William D. Bowers and U.S. Pat. No. 4,871,984 issued Oct. 3, 1989 to Laton et al., both of which are hereby incorporated by reference as though fully disclosed herein.

Figure 4:
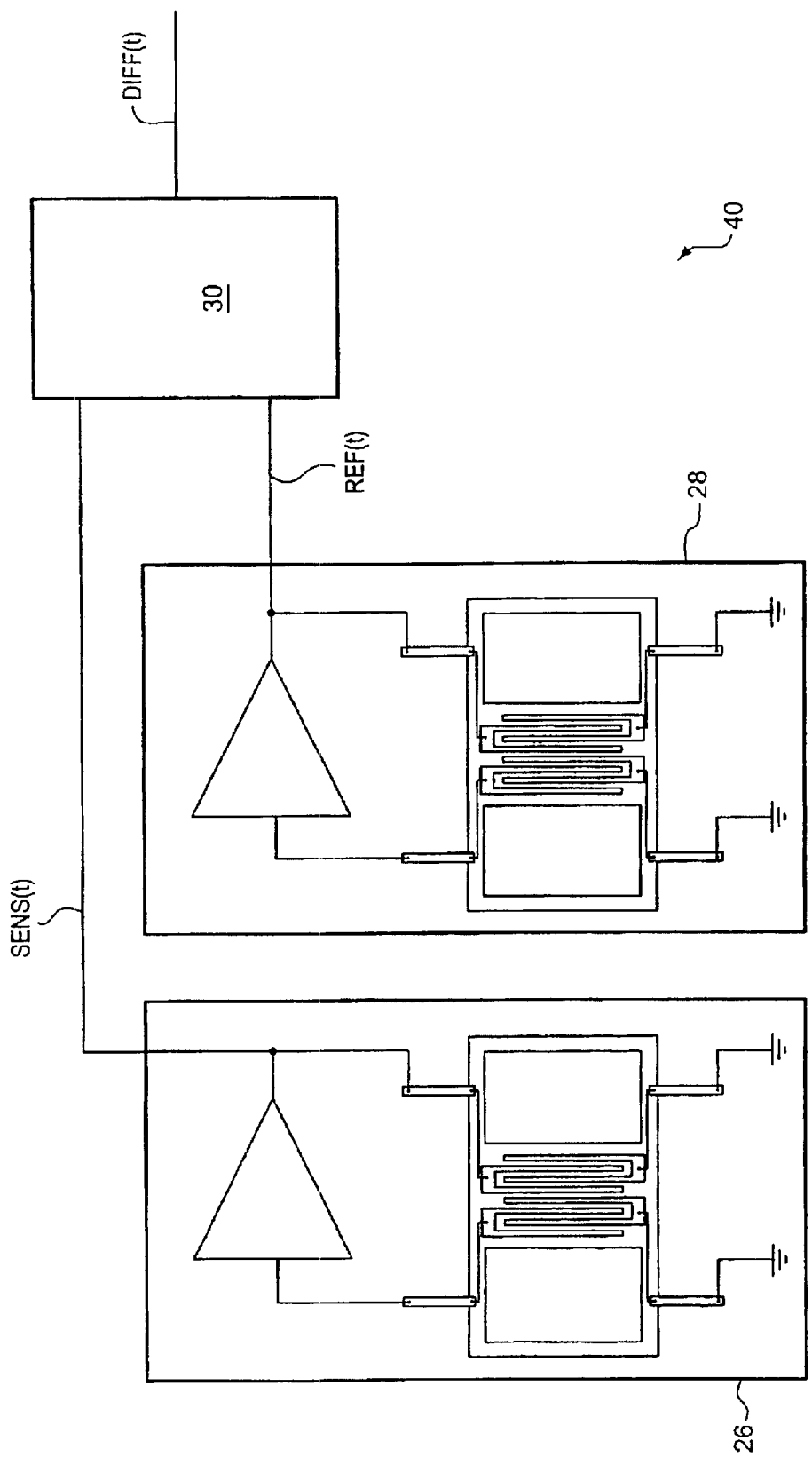
FIG. 4 shows an example reactive detection apparatus according to FIG. 2 further including a reference SAW.

FIG. 4 shows a preferred embodiment of a molecular contamination monitor 40 according to the invention. Monitor 40 comprises a detection surface SAW sensor 26 as described in reference to FIG. 1 having a film such as item 20 exposed to an ambient fluid, and a reference SAW device 28, substantially identical to the FIG. 1 SAW device, preferably mounted in a hermetic chamber as known in the art. A comparator 30 receives the oscillating signal SENS(t) from the detection surface SAW sensor 26 and the oscillating signal REF(t) from the reference SAW device 28 and generates difference signal DIFF(t) representing the frequency difference, sometimes referred to as the beat frequency in the art. The value of DIFF(t) corresponds to the increased mass on the film (such as item 20) on the SAW 26. This frequency is on the order of half a megahertz, ranging typically from 0.3 MHz to 0.8 MHz. The data disclosed in FIGS. 5–11 below were all obtained from a molecular contamination monitor 40 as shown in FIG. 4.

Temperature regulation of the FIG. 1 SAW apparatus is a further contemplated feature of the invention, using, for example, a temperature regulator located proximal to the SAW 2 as disclosed in the Bowers patent mentioned above.

Further aspects and features of the invention include using a plurality of sensing SAWs such as that depicted in FIG. 1 to simultaneously monitor different critical surface materials. It is also contemplated that higher frequency (more sensitive) SAW crystals, up to 1 GHz or more, may be used.

Figure 5:
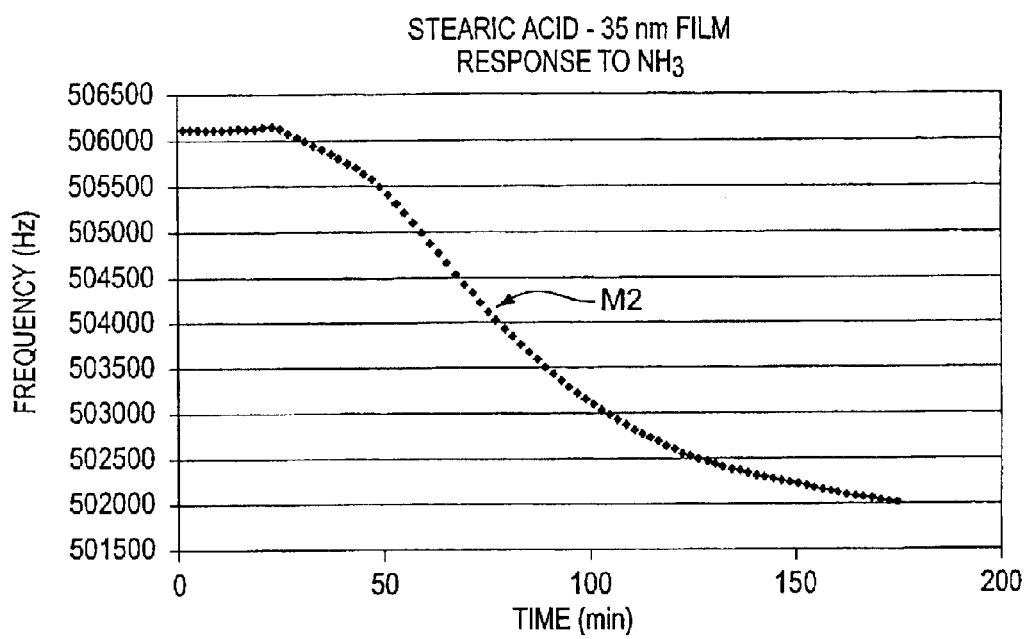
FIG. 5 is a measurement plot showing an observed frequency versus time characteristic of a SAW coated according to a first aspect of the invention and exposed to ammonia.

FIG. 5 is a measurement plot showing an observed frequency in hertz versus time in minutes curve characteristic of a SAW substrate coated with a film of stearic acid, having a 35 nm thickness, when exposed to ammonia. Stearic acid is an equivalent surface for the acid catalyst component of a photoresist. The SAW was connected within a free-running oscillator circuit exhibiting an initial oscillating frequency of 0.506 MHz or 506 KHz. The SAW was exposed to ammonia ($NH_3$) vapor, at a concentration of one part per million. After a 50-minute exposure, the frequency had decreased to 0.505 MHz, continuing to decrease monotonically along the depicted measurement trajectory M2 until, after a 170-minute exposure, the frequency had decreased to approximately 0.502 MHz. The total frequency change is seen as 400 kHz. As is seen in FIG. 5, the observed rate of frequency change, although monotonically decreasing, was not fully linear.

Figure 6:
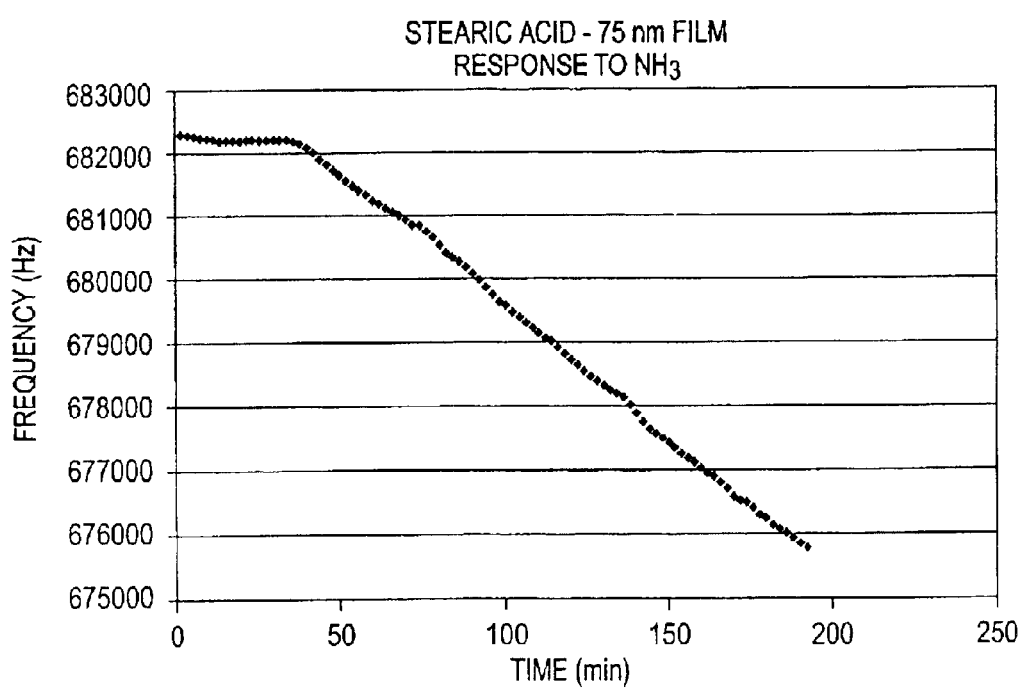
FIG. 6 is a measurement plot showing an observed frequency versus time characteristic of a SAW coated as that of the FIG. 5 measurement, but with a different coating thickness.

FIG. 6 is a measurement plot showing an observed frequency versus time characteristic of a SAW coated with a film substantially identical to that for the FIG. 5 measurement, but with a film thickness of 75 nm. As can be seen, the film coating of different coating thickness produced a frequency change that was substantially linear over a 200-minute observation. The total frequency change over the 200-minute observation was 7 kHz.

Figure 7:
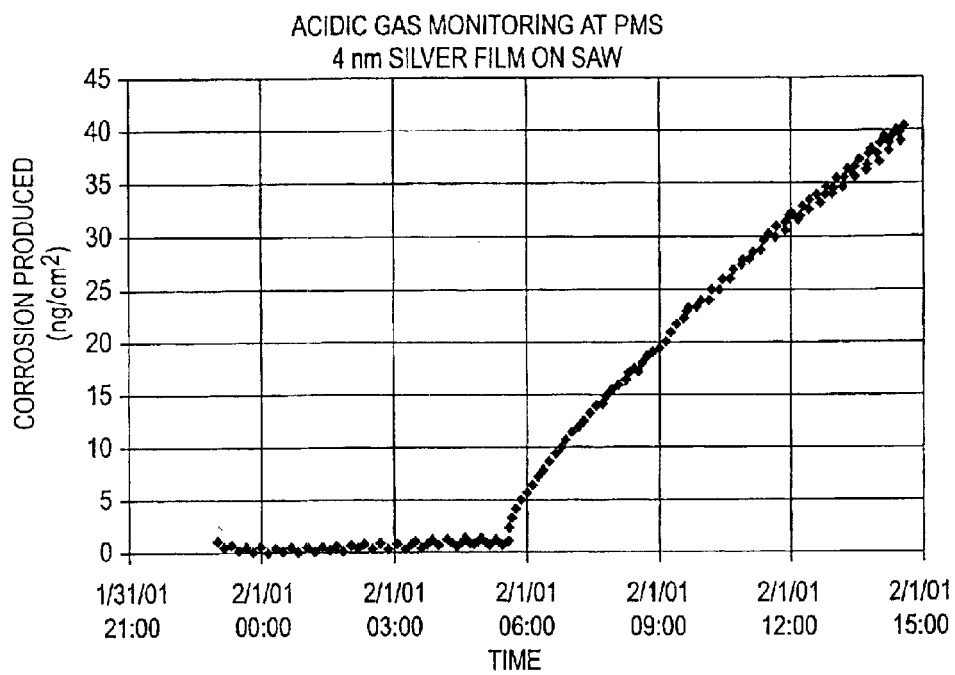
FIG. 7 is a measurement plot showing corrosion mass accumulation with respect to time on a SAW coated with silver according to the invention.

FIG. 7 is a measurement plot showing corrosion mass accumulation in nanograms per centimeter squared ($ng/cm^2$) with respect to time on a SAW coated with silver according to this invention. The SAW from which the FIG. 7 measurements were obtained comprised a substrate corresponding to item 4A of FIG. 1, coated with a silver film corresponding to item 20, with a thickness equal to 4 nm. The SAW was connected within a free-running oscillator circuit 21 and exhibited an initial oscillating frequency of 199.5 MHz, with measurement beginning at a time labeled "0:00, Feb. 1, 2001". At a time just prior to "6:00" on "Feb. 1, 2001", the upper surface of the silver film was exposed to acidic gas, namely sulfur dioxide at a concentration of about 75 parts per billion. The vertical axis of FIG. 6 is in units of nanograms per centimeter squared, or "$ng/cm^2$". A conversion factor of 0.020 nanograms per centimeter squared per hertz was used to convert from the measured oscillating frequency to the depicted units of "$ng/cm^2$".

Figure 8:
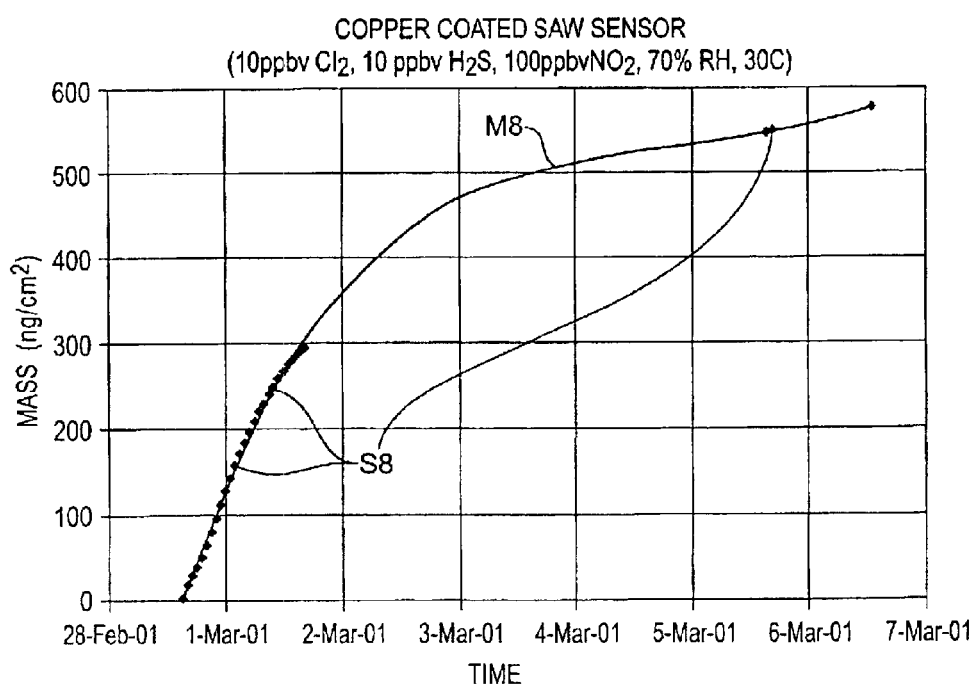
FIG. 8 is a measurement plot showing mass accumulation with respect to time on a SAW coated with copper according to the invention.

FIG. 8 is a measurement plot showing corrosion mass accumulation with respect to time on a SAW substantially identical to that measured for FIG. 7, coated with copper instead of silver. The SAW was connected within a similar free-running oscillator circuit, exhibiting an initial oscillating frequency of 199.5 MHz. The vertical axis of FIG. 8 is in the same units of nanograms per centimeter squared, or "$ng/cm^2$", as FIG. 7, arrived at using the same conversion factor of 0.020 nanograms per centimeter squared per hertz. The test environment for the FIG. 8 measurement was air at 70% relative humidity, 30° C., having the following contaminants:

| Compound | Concentration (parts per billion volume) |
|---|---|
| $Cl_2$ | 10 |
| $H_2S$ | 10 |
| $NO_2$ | 100 |

The measurement plot, labeled M8, was constructed using a best fit through sample points S8.

Figure 9:
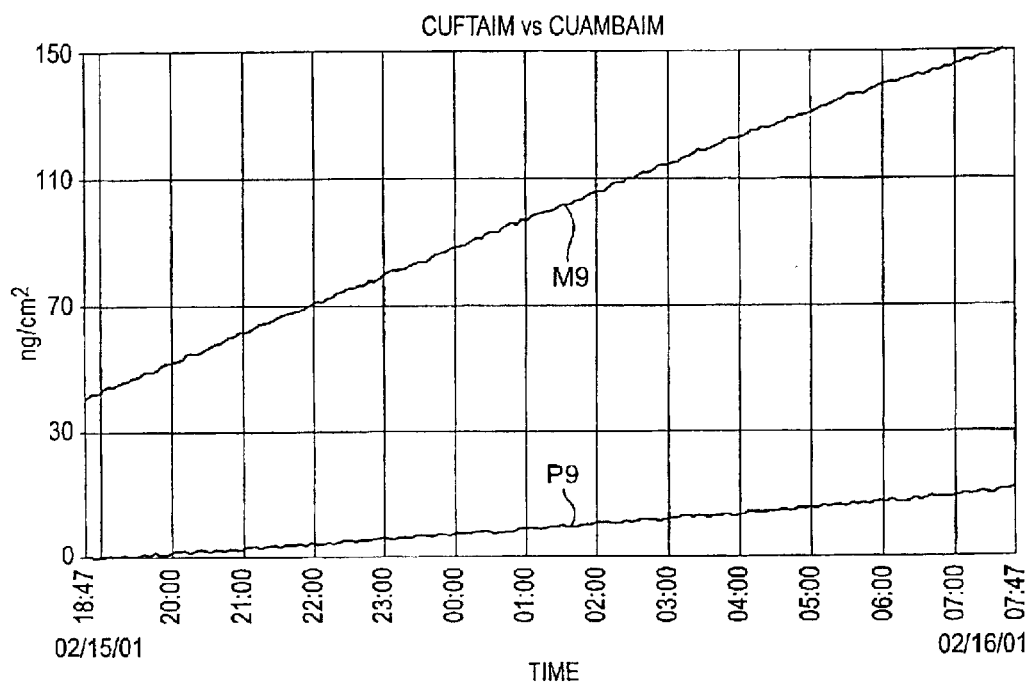
FIG. 9 shows a comparison between a sensitivity of a SAW device coated according to the present invention and a conventional SAW.

FIG. 9 shows a comparison plot of mass accumulation in $ng/cm^2$ versus time in hours between a sensitivity of a SAW device coated according to the present invention, which is the M9 plot line, and a conventional SAW, which is the P9 plot line.

Figure 10:
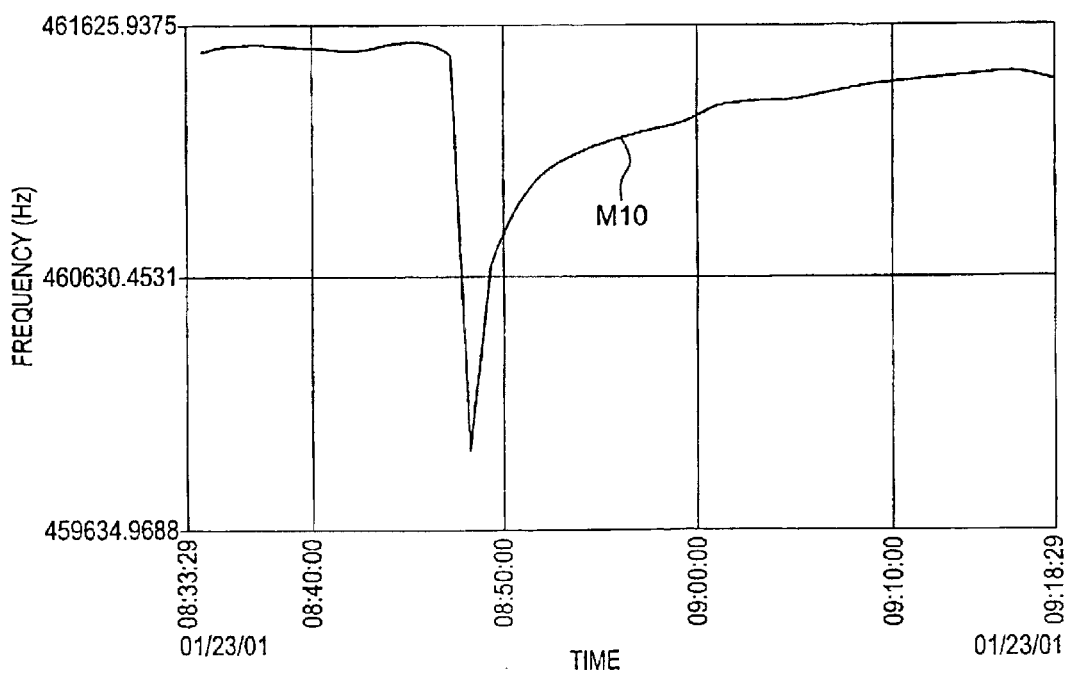
FIG. 10 is a measurement plot showing a frequency shift of a SAW device coated according to the present invention exposed to a limited duration of ammonia.

FIG. 10 shows a measurement plot M10 of frequency in hertz versus time representing a frequency shift of a SAW device coated with a film of stearic acid exposed to a pulse of ammonia.

Figure 11:
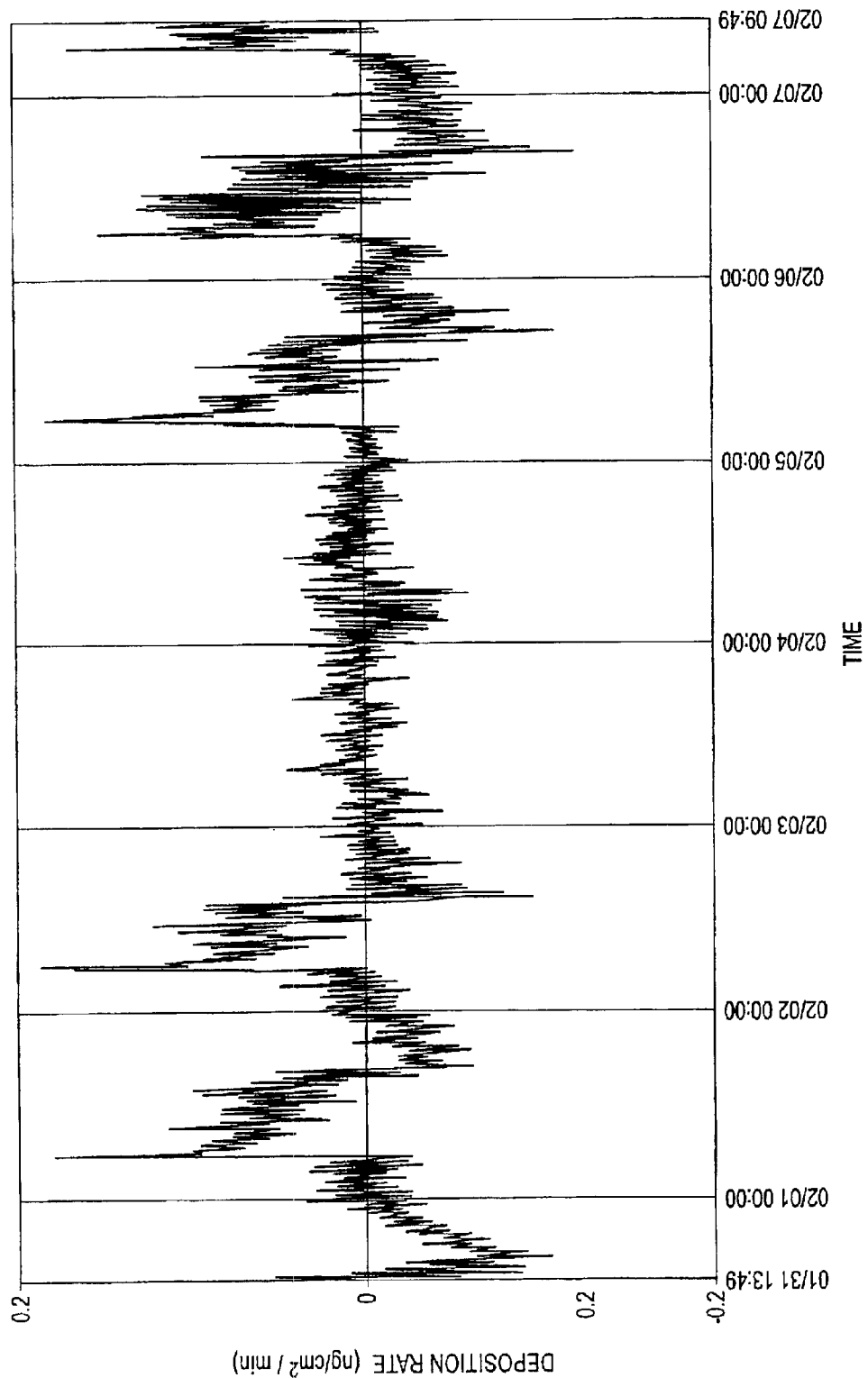
FIG. 11 shows a plot of an example measurement of a rate-of-change of frequency obtained from a SAW coated according to the present invention.

FIG. 11 shows a plot of an example measurement of deposition rate in $ng/cm^2$/minute versus time over an eight-day period obtained from a SAW coated with a silver film. The peaks on the $2^{nd}$, $3^{rd}$, and $6^{th}$ through $8^{th}$ days coincided with a diesel generator being run outside the building in which the measurement was being made.

One advantage of the present invention is that it provides unique information about chemical and physical processes that occur on critical surfaces.

The surface acoustic wave device according to this invention provides real-time observations of the impact of airborne molecular contaminants (AMC) on surfaces using a more direct approach than air sample monitoring, and a mass sensitivity more than 100 times greater than existing quartz crystal microbalance (QCM) technologies. By mimicking specific critical surfaces, where the effect of AMC occurs, many sources of error are eliminated including: estimation of species specific sticking coefficients, sticking coefficient variations due to temperature and humidity changes, and synergistic chemical interactions on the target surface.

It should be understood that the particular embodiments shown in the drawings and described within this specification are for purposes of example and should not be construed to limit the invention which will be described in the claims below.

What is claimed is:

1. A device for monitoring spontaneous molecular contamination on a subject surface susceptible to degradation by a molecular contaminant, said device comprising:

a surface acoustic wave (SAW) device having a SAW measurement surface, said SAW device including an electrical circuit for providing an output signal indicative of spontaneous molecular contamination on said measurement surface in an amount equal to 100 $ng/cm^2$ or less; and said SAW measurement surface including a coating that is equivalent to said subject surface with respect to said spontaneous contamination by a molecular contaminant.

2. A molecular contamination monitor as in claim 1 wherein said coating comprises essentially the same material as said subject surface.

3. A molecular contamination monitor as in clam 1 wherein said coating comprises a material that interacts chemically with said contaminant in an equivalent manner to said subject surface.

4. A molecular contamination monitor as in clam 1 wherein said coating is a photoresist or chemical equivalent.

5. A molecular contamination monitor as in claim 1 wherein said coating is metallic.

6. A molecular contamination monitor as in claim 5 wherein said SAW includes a transducer, said coating overlays said transducer, and said molecular contamination monitor includes an insulating film disposed between said transducer and said coating such that said coating is not in electrical contact with said transducer.

7. A molecular contamination monitor as in claim 5 wherein said coating comprises a metal selected from the group consisting of copper, silver, gold, platinum, titanium, tungsten, aluminum and nickel.

8. A molecular contamination monitor as in claim 1 wherein said coating comprises a metal oxide.

9. A molecular contamination monitor as in claim 1 wherein said coating comprises a semiconductor material.

10. A molecular contamination monitor as in claim 9 wherein said SAW includes a transducer, said coating overlays said transducer, and said molecular contamination monitor includes an insulating film disposed between said transducer and said coating such that said coating is not in electrical contact with said transducer.

11. A molecular contamination monitor as in claim 9 wherein said coating comprises a material selected from the group consisting of silicon, gallium arsenide, gallium nitride, germanium, and silicon germanium.

12. A molecular contamination monitor as in claim 1 wherein said coating comprises a material selected from the group consisting of silicon dioxide, silicon nitride, and glass.

13. A molecular contamination monitor as in claim 1 wherein said coating comprises stearic acid.

14. A molecular contamination monitor as in claim 1 wherein said coating comprises a thin film.

15. A molecular contamination monitor as in claim 1 wherein said amount is 60 ng/cm$^2$ or less.

16. A molecular contamination monitor as in claim 1 wherein said amount is 30 ng/cm$^2$ or less.

* * * * *